United States Patent [19]
Vinegar et al.

[11] Patent Number: 6,094,048
[45] Date of Patent: Jul. 25, 2000

[54] NMR LOGGING OF NATURAL GAS RESERVOIRS

[75] Inventors: Harold J. Vinegar, Houston, Tex.; Ridvan Akkurt, Mandeville, La.; Pierre Nazareth Tutunjian, Houston, Tex.

[73] Assignee: Shell Oil Company, Houston, Tex.

[21] Appl. No.: 08/993,138

[22] Filed: Dec. 18, 1997

Related U.S. Application Data

[60] Provisional application No. 60/032,498, Dec. 18, 1996.

[51] Int. Cl.[7] ................................................ G01V 3/00
[52] U.S. Cl. ........................................................ 324/303
[58] Field of Search .................................. 324/303, 300, 324/307, 309, 312, 314

[56] References Cited

U.S. PATENT DOCUMENTS

| | | | |
|---|---|---|---|
| 4,424,487 | 1/1984 | Lauffer | 324/307 |
| 4,710,713 | 12/1987 | Strikman | 324/303 |
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,719,423 | 1/1988 | Vinegar et al. | 324/303 |
| 5,023,551 | 6/1991 | Kleinberg et al. | 324/303 |
| 5,212,447 | 5/1993 | Paltiel | 324/300 |
| 5,280,243 | 1/1994 | Miller | 324/303 |
| 5,285,158 | 2/1994 | Mistretta et al. | 324/309 |
| 5,289,127 | 2/1994 | Doddrell et al. | 324/314 |
| 5,291,137 | 3/1994 | Freedman | 324/303 |
| 5,309,098 | 5/1994 | Coates et al. | 324/303 |
| 5,497,087 | 3/1996 | Vinegar et al. | 324/303 |
| 5,498,960 | 3/1996 | Vinegar et al. | 324/303 |
| 5,696,448 | 12/1997 | Coates et al. | 324/303 |

FOREIGN PATENT DOCUMENTS 2 276 007A  9/1994  United Kingdom.

OTHER PUBLICATIONS

R. Chandler et al., SPE Paper 28365, "Improved Log Quality with a Dual–Frequency Pulsed NMR Tool," Jun. 16, 1994.

Dawson et al., AIChE Journal, V. 16, No. 5, p. 726 (Sep. 1970).

Schlumberger Log Interpretation Principals/Applications (*1987*), Schlumberger Educational Services, Houston, Texas, Figs. 5–17, p. 45.

C. J. Gerritsma et al., "Proton–Spin–Lattice Relaxation and Self–Diffusion in Methanes—Paper 2," *Physica*, V. 51, 392 (1971).

G. R. Coates et al., SPE Paper 22723, "The Magnetic Resonance Imaging Log Characterized by Comparison With Petrophysical Properties and Laboratory Core Data." Paper presented at 66th Annual Technical Conference and Exhibition of the Society of Petroleum Engineers, Dallas, Tex., Oct. 6–9, 1991.

*Primary Examiner*—Louis Arena
*Attorney, Agent, or Firm*—Del S. Christensen

[57] ABSTRACT

A method is provided to estimate the pore volume of a formation occupied by hydrocarbon phase or phases, the method comprising the steps of: obtaining a first pulsed NMR log of the formation, the pulse sequence of the first NMR log comprising an initial 90° radio frequency pulse, followed by a series of 180° radio frequency pulses starting at a time period $t_{cp1}$ after the initial 90° pulse, and the series of pulses comprising magnetic pulses each separated by a time period $2t_{cp1}$; obtaining a second pulsed NMR log of the formation, the pulse sequence of the second NMR log comprising an initial 90° radio frequency pulse, followed by a series of 180° pulses starting at a time period $t_{cp2}$ after the initial 90° pulse, and the series of 180° pulses comprising radio frequency pulses each separated by a time period $2t_{cp2}$ wherein the time $t_{cp2}$ is a time that is different from $t_{cp1}$ by an amount of time sufficient to separate resultant peaks of transverse relaxation times attributable to the hydrocarbon phase or phases within the formation; and determining, from the first and the second NMR logs, the pore volume of a formation occupied by hydrocarbon phase or phases within the formation. In a preferred embodiment, pore volume occupied by hydrocarbon gas is determined, and $t_{cp2}$ is a time that is greater than that which results in the measured transverse relaxation time of the hydrocarbon gas being less than about $2\times10^{-3}$ seconds and $t_{cp1}$ is a time that is less than that which results in the measured transverse relaxation time of the hydrocarbon gas being greater than about $4\times10^{-3}$ seconds.

29 Claims, 3 Drawing Sheets

6,094,048

NMR LOGGING OF NATURAL GAS RESERVOIRS

This application claims the benefit of U.S. Provisional Application No. 60/032,498, filed Dec. 18, 1996, the entire disclosure of which is hereby incorporated by reference

FIELD OF THE INVENTION

The invention relates to nuclear magnetic resonance logging of formations to estimate hydrocarbon content of the formation.

BACKGROUND TO THE INVENTION

In the exploitation of hydrocarbon reservoirs, use is made of well logging to determine the amount of recoverable hydrocarbons. Logging tools such as density, neutron, and resistivity logs, have been developed for measurement of reservoir properties such as porosity and water and hydrocarbon saturation of pore space. These tools are widely utilized in the oil industry. However, in order to accurately determine porosity using these tools, the lithology of the rock must be known. Many other rock and fluid properties, such as salinity, cementation factor, saturation exponent, and shaliness, must be known from sources such as resistivity logs to determine hydrocarbon saturation. In addition, methods are not known for estimating pore size or permeability in a continuous log, i.e. without taking fluid samples.

Nuclear Magnetic Resonance ("NMR") well logging tools capable of determining the liquid contents of pore volume within a reservoir, and a method to use these tools are described in, for example, U.S. Pat. Nos. 5,309,098, 5,291,137, 5,280,243, 5,212,447, 4,717,878, 4,717,877, 4,717,876, and 4,710,713. In particular, U.S. Pat. No. 5,291,137 discloses a Carr-Purcell-Meiboom-Gill ("CPMG") pulse sequence and echo response and a method to obtain free fluid porosity, total NMR porosity, bound fluid porosity, spin-spin or transverse relaxation time ($T_2$) (which is related to pore size distribution in sandstone), and continuous permeability logs. Recovery times between CPMG pulse trains is typically between 0.5 and 1.5 seconds. Because the spin lattice or longitudinal relaxation time $T_1$ of methane in typical reservoir conditions is greater than about three seconds, the total NMR porosity measured in this method could not include the volume occupied by hydrocarbon gas.

Recently, a new logging tool, the MRIL (TM NUMAR Corp. of Malvern, Pa.) has been introduced for determining the liquid-filled porosity in a lithology independent manner, i.e. the tool response does not require a lithology correction to determine porosity. The MRIL uses pulsed nuclear magnetic resonance of the mobile protons in the pore space. However, according to the tool's manufacturer, this tool is not capable of measuring the hydrocarbon gas content of the pore space.

This inability to detect gas has been a major disadvantage because the main or only hydrocarbon in many reservoirs is natural gas. The pore fluids in these reservoirs consist of only brine and natural gas. The inability to measure gas means that the NMR logging tool will not measure gas-filled porosity and must rely on comparison with other logging tools, such as density and neutron logs, to measure porosity.

It is therefore an object of the present invention to provide a method to determine the hydrocarbon content within a formation using a nuclear magnetic resonance ("NMR") log wherein formation properties, other than pore pressure and temperature, do not have to be known. It is another object of the present invention to provide a method to determine the hydrocarbon content that is not affected by the formation's clay content. It is a further object to provide such a method wherein the method is less susceptible to errors due to noise in the NMR log.

SUMMARY OF THE INVENTION

These and other objects are accomplished by a method to estimate the pore volume of a formation occupied by hydrocarbon phase or phases utilizing a NMR logging tool, the method comprising the steps of:

obtaining a first pulsed NMR log of the formation, the first NMR log utilizing a pulse sequence comprising an initial 90° radio frequency pulse, followed by a series of 180° radio frequency pulses starting at a time period $t_{cp1}$ after the initial pulse, and the series of 180° radio frequency pulses comprising 180° radio frequency pulses each separated by a time period $2t_{cp1}$ wherein the time $t_{cp1}$ is a time which results in the measured transverse relaxation time of the hydrocarbon phase or phases being within a range of measured transverse relaxation times that are detectable with the NMR logging tool utilized;

obtaining a second pulsed NMR log of the formation, the pulse sequence of the second NMR log comprising an initial 90° radio frequency pulse, followed by a series of 180° radio frequency pulses starting at a time period $t_{cp2}$ after the initial 90° pulse, and the series of pulses comprising 180° radio frequency pulses each separated by an interecho time period $2t_{cp2}$ wherein the time $t_{cp2}$ is a time that is different from $t_{cp1}$ by an amount of time sufficient to separate resultant peaks of transverse relaxation times attributable to hydrocarbon phase or phases within the formation between the two logs; and determining from the first and the second NMR logs the pore volume of a formation occupied by hydrocarbon phase or phases.

In a preferred embodiment, formation porosity containing hydrocarbon gas is determined.

By adjusting the interecho time ($2t_{cp}$) of the NMR pulse sequence (a CPMG sequence) the transverse relaxation time $T_2$ of the hydrocarbon is significantly altered because of the strong dependence of $T_2$ on diffusional relaxation for gases. Liquid water, whether bound or free, is much less influenced by diffusion as a method of relaxation and therefore have NMR responses to CPMG sequences that are not significantly affected by altering the interecho time of the CPMG pulse sequence. A $T_2$ of less than about two milliseconds cannot be detected by current commercial NMR logging tools. Therefore logs using an interecho time sufficiently long that $T_2$ is less than two milliseconds will not indicate any peaks attributable to hydrocarbon gas. The difference between the NMR detected porosity of one such log using a long interecho time and another having an interecho time sufficiently short that $T_2$ is detected will therefore directly relate to gas-filled porosity. Similarly, a longer $t_{cp}$ can be utilized, the longer $t_{cp}$ resulting in both the liquid hydrocarbon phase, and the gas hydrocarbon phase being below deductibility, resulting in only the water-filled porosity being detected. Therefore either the liquid hydrocarbon, the hydrocarbon gas, or both can be determined by the differences between two NMR logs, the two NMR logs being run with differing $t_{cp}$s.

Current commercial NMR logging tools also have a lower limit of interecho times of about one millisecond. Use of an interecho time at about this lower limit results in hydrocarbon gas peaks of about forty milliseconds (for a magnetic field gradient of 17 gauss/cm). Utilization of shorter interecho times could further separate gas peaks from peaks attributable to liquids, and could be advantageous if a logging tool were to become available with such capabilities. The method of the present invention can be utilized to determine gas content of formations even with interecho times greater than one millisecond because, although hydrocarbon gas peaks may over-lap peaks from bound liquids, the differences between the peaks from the two logs would still indicate the amount of hydrocarbon gas present in the formation.

DETAILED DESCRIPTION OF THE INVENTION

The NMR log of the present invention is altered from that typically used in oil industry well logging by manipulation of the interecho time to change the response of hydrocarbon gas to the pulse sequence. A CPMG echo sequence with phase alteration of the 90° radio frequency pulses, such as is disclosed in U.S. Pat. No. 5,291,137 is utilized, along with a NMR logging tool such as the MRIL C available from NUMAR Corp. of Malvern, Pa. The NMR logging tool preferably is a tool that utilizes a magnetic gradient. The gradient of the MRIL C tool is about 17 gauss/cm. The gradient may be a pulsed or a fixed gradient. Such gradients are typically induced by magnets within the logging tool, but internal rock gradients may possibly be utilized. The MRIL tool is capable of sensing properties of a portion of a formation that is as much as four or five inches from the wellbore wall. A tool such as the MRIL C is therefore preferred in the practice of the present invention. This is preferred because rocks within less than two or three inches from the wellbore wall may be contaminated with drilling fluids and not at all representative of the formation in general. With the MRIL-C tool the two logs can be obtained on the same pass. MRIL-C tool has two different annuli located slightly apart from the other. These two different annuli can be activated with two different pulse sequences.

Figure 2:
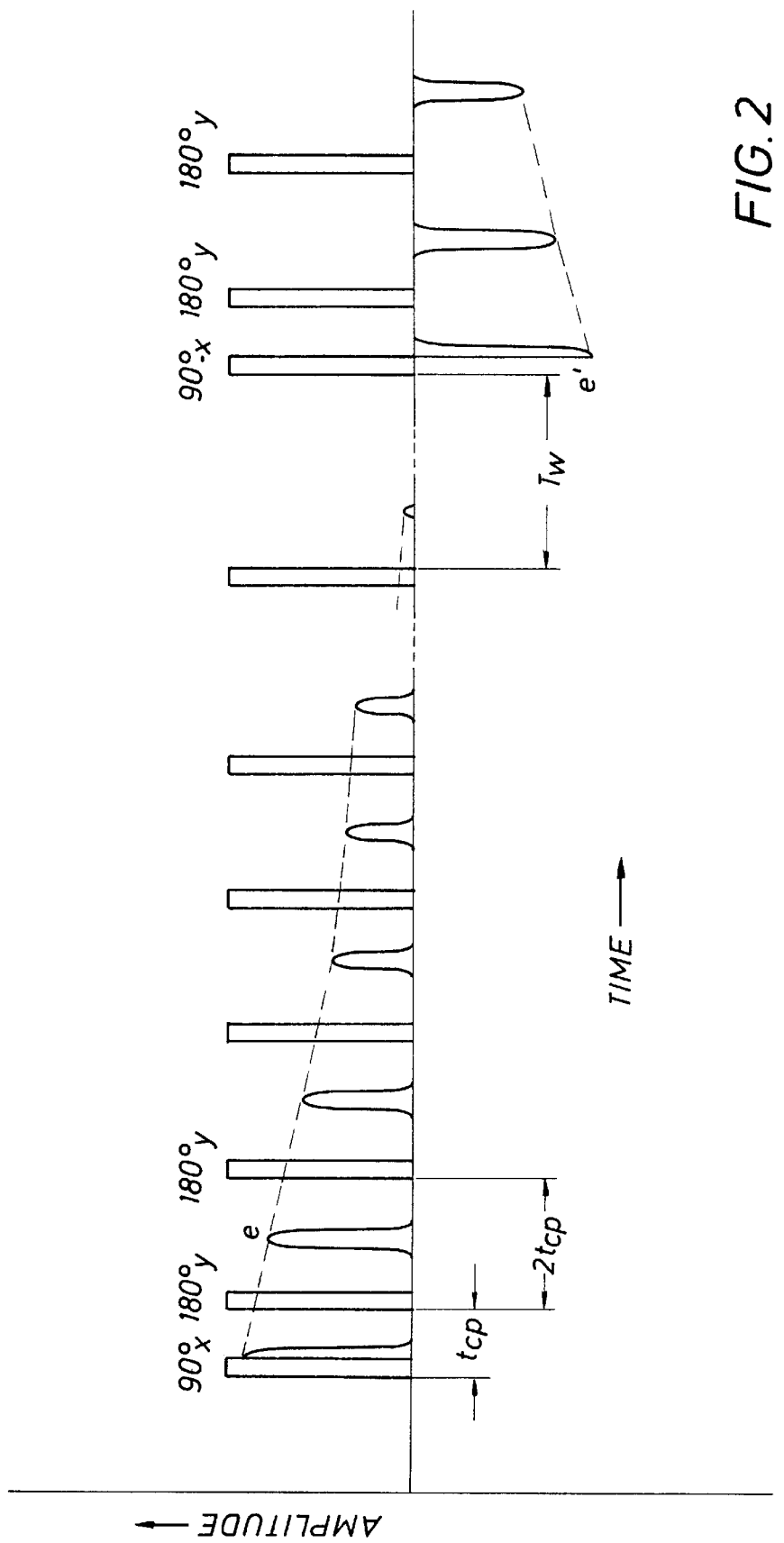
FIG. 2 shows a typical CPMG echo sequence (with phase alternation of the 90° pulse) used for measuring transverse relaxation time, $T_2$.

Referring now to FIG. 2, an exemplary CPMG pulse sequence with phase alternation of the 90° pulse is shown. This pulse sequence is used for measuring a distribution of transverse relaxation times, $T_2$. The sequence consists of a 90-degree radio frequency pulse (at the Larmor frequency), followed at time $t_{cp}$ by a train of equally spaced 180-degree pulses. The spacing of the 180-degree pulses is $2t_{cp}$. For example in the MRIL C this time can be as short as 1.2 ms. A spin echo, e, is obtained between each of the 180-degree pulses. The sequence is repeated after a wait time $T_W$ with a 90° radio frequency pulse of opposite phase (relative to the preceding 90° radio frequency pulse). The subsequent train of negative echos, e', is subtracted from the previous train thus building up coherent signals and canceling instrument artifacts.

When there are multiple fluids in the pore space, and a range of pore sizes, the NMR signal as a function of time, A(t), represents a sum of exponential decays:

$$A(t) = \sum_{i=0}^{n} a_i e^{-t/T_{2i}} \quad (1)$$

where $a_i$ is a constant, $T_{2i}$ is a constant representative of a relaxation time and n is an integer wherein n $T_{2i}$s are selected at equal logarithmic intervals. Typically, thirty five to fifty intervals, n, result in an acceptable fit to echo data. The time domain data can be inverted using a multiexponential inversion program yielding a histogram, or a plot of $a_i$ as a function of $T_{2i}$. This inversion is discussed in, for example, U.S. Pat. No. 5,291,137. A multiexponential inversion of an echo train from a NMR response such as that displayed in FIG. 2 can therefore be expressed as a $T_2$ relaxation time distribution. The ordinate would be the signal amplitude associated with each $T_{2i}$ time constant by fitting $a_i$ for the given sets of $T_{2i}$s. NMR pore volumes can be determined by the integral of $a_i$ with respect to $T_2$, and application of a constant determined from calibration, and multiplication with an effective hydrogen index.

Relaxation times of components that are bound to solids are generally significantly shorter than components that are not bound to solids. Surfaces in formations are generally either water or oil wet but are not gas wet. Thus, surface relaxation effects are negligible for gases.

Natural gas is composed predominantly of methane and light alkanes. Typically, over 75% by volume of dry gas is methane. Properties of the hydrocarbon gas within a formation can therefore be estimated with sufficient accuracy for the practice of the present invention by assuming a hypothetical hydrocarbon such as a $C_{1.1}H_{4.2}$ hydrocarbon composition.

Longitudinal relaxation times, $T_1$, of gases such as methane are solely a function of temperature and pressure, and not of other properties of the formation. $T_1$ for methane is discussed in, for example, C. J. Gerritsma, et al., "Proton Spin Lattice Relaxation and Self Diffusion in Methanes-Paper 2", Physica, v. 5, 392 (1971). $T_1$ is considered to be proportional to the density and to vary with absolute temperature according to:

$$\ln(T_1) = a - b\left(\frac{1}{T}\right) \quad (2)$$

where: a and b are constants and T is the absolute temperature.

Figure 1:
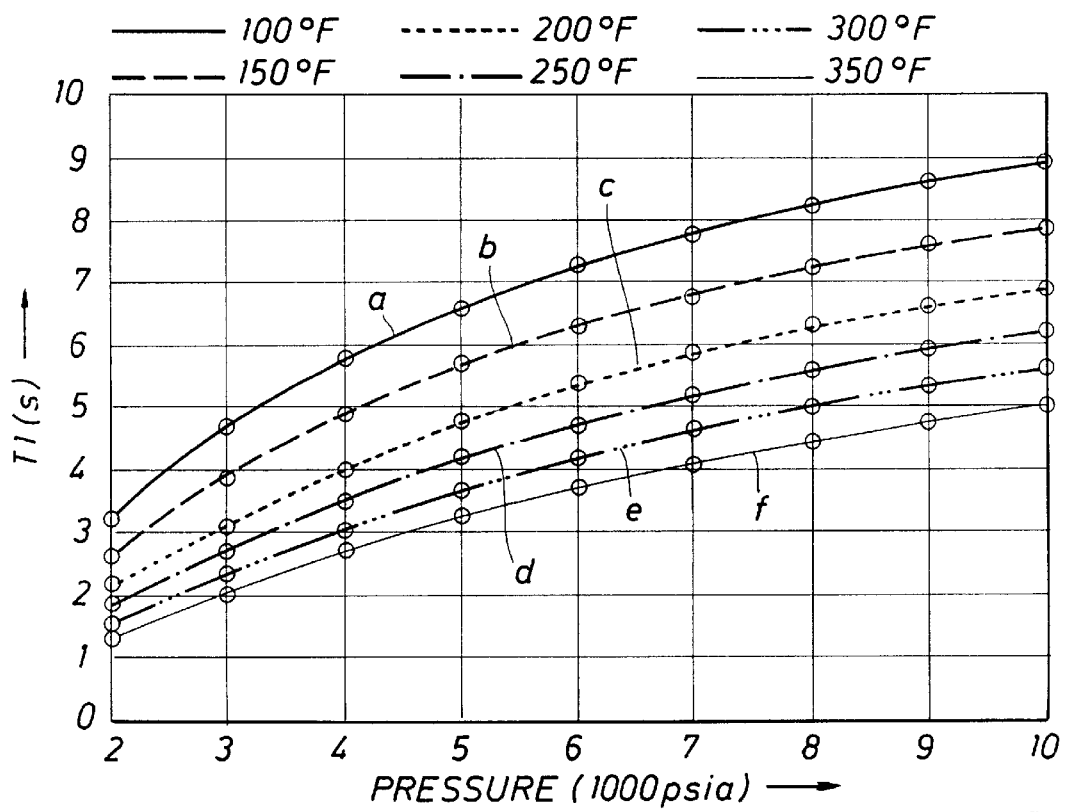
FIG. 1 is a plot of $T_1$ of methane as a function of pressure for different temperatures.

Referring now to FIG. 1, a plot of $T_1$ for a natural gas having a composition of $C_{1.1}H_{4.2}$ is shown as a function of pressure for different temperatures. Equation 2 can be used to extrapolate $T_1$ data for methane and hydrocarbon gas compositions to other temperatures. Lines a through f represent $T_1$, in seconds, for temperatures of 100° F. through 350° F. in fifty degree increments, respectively.

As an example of typical reservoir conditions, methane may have a density of about 0.2 g/cc and a temperature of about 200° F., resulting in a $T_1$ of about four seconds. A wait time of six seconds will generally exceed $T_1$, and result in a NMR log that is useful in the practice of the present invention. Thus in order not to completely saturate the signal from methane the wait time ($T_W$) in the CPMG sequence (the time between the last 180° pulse and the next initial 90° pulse of the CPMG sequence) should be greater than four seconds, and preferably between about six and twelve seconds which is two to three times the $T_1$ of gas. $T_1$ of natural gas is between about 3 and 6 seconds for typical reservoir conditions.

In FIG. 2, the sequence is repeated after a wait time, $T_W$. If $T_W$ is greater than three times $T_1$, then almost complete relaxation will occur. If $T_W$ is not significantly greater than $T_1$, a correction factor, $\alpha$, is applied to account for partial saturation. This correction is given by:

$$\alpha = \left(1 - e^{-\frac{T_W}{T_1}}\right) \quad (3)$$

Both logs of the present invention can be performed using a $T_W$ significantly longer than $T_1$ so that substantial corrections for partial saturation will not have to be made. It is preferred that $T_W$ of the two logging runs be the same but it is not necessary that they be the same. $T_W$ for the log using a longer $t_{cp}$ can be made using a relatively short $T_W$ with respect to the gas $T_1$ (i.e., $T_W$ less than $T_1$ of the hydrocarbon gas at formation conditions). The short $T_W$ also suppresses the NMR response of the gas along with the suppression of the NMR response of the gas due to the changed $t_{cp}$.

NMR logging is normally restricted to measuring hydrogen ($^1$H) because of its strong signal and high gyromagnetic ratio. Log results must therefore be corrected for hydrogen density to determine pore volumes. The hydrogen index, HI, is defined as the density of hydrogen atoms relative to liquid water at saturated conditions, and the HI is typically used to convert NMR porosities (raw results) to actual pore volumes. HI for hydrocarbon gases are known and available in, for example, *Schlumberger Log Interpretation Principals/Applications*, (1987), available from Schlumberger Educational Services, Houston, Tex., and in particular, FIGS. 5–17, p. 45, wherein density and HI of natural gas slightly heavier than methane ($C_{1.1}H_{4.2}$) are shown as a function of pressure and temperature. Under typical reservoir conditions, the gas pressure will be between about 2000 and 10,000 psi and the temperature will be between about 100° F. and about 350° F., resulting in gas densities between about 0.1 and 0.3 g/cc and a HI between about 0.2 and about 0.6. Although this HI is less than one, it is still sufficiently large and renders the hydrocarbon gas measurable with the NMR pulse sequence of the present invention.

Figure 3:
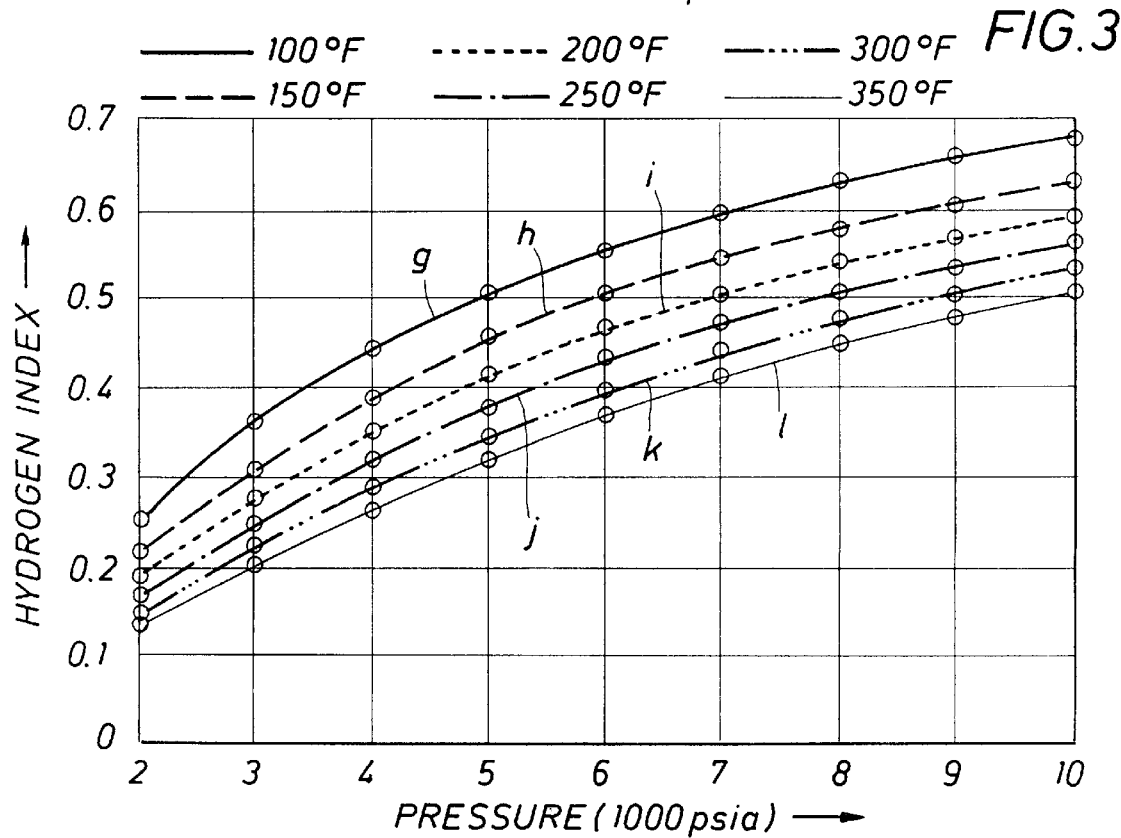
FIG. 3 is a plot of hydrogen index for natural gas as a function of pressure for different temperatures.

Referring now to FIG. 3, a plot is shown of HI for a natural gas having a composition of $C_{1.1}H_{4.2}$ as a function of pressure for different temperatures. Lines g through l represent HI at temperatures of 100° F. through 350° F. in fifty degree increments respectively.

The "effective HI" is referred to herein as the product of $\alpha$ and HI.

The relaxation mechanisms that affect $T_1$ and $T_2$ in rocks are (1) molecular motion in fluids, (2) surface relaxivity at the pore wall, and (3) molecular diffusion in magnetic field gradients.

The first mechanism, due to local motions such as molecular tumbling, is called bulk relaxation. Longitudinal relaxation times and transverse relaxation times are equal when the predominant relaxation mechanism is bulk relaxation, i.e., $T_{1B} \approx T_{2B}$. Bulk relaxation is the predominant relaxation mechanism for non-wetting phases, i.e., $T_1 = T_{1B}$.

The second relaxation mechanism is surface relaxation at the pore wall, or the relaxation of $^1$H nuclei when they closely approach paramagnetic ions such as iron and manganese which reside on grain surfaces. This is the dominant mechanism for fluid molecules such as water that wet the rock surfaces. However, because gas is always non-wetting and never closely approaches the rock surface, this mechanism is negligible for gas. This provides a major advantage in the practice of the present invention in that only one relaxation time is measured for the gas, not a distribution of relaxation times that is a function of surface properties of the rock.

The third relaxation mechanism is the diffusion of molecules in magnetic field gradients. This relaxation mechanism affects only $T_2$ and not $T_1$. Therefore, when diffusion is a prominent relaxation mechanism, $T_2$ will be substantially less than $T_1$. Diffusion is the predominant relaxation mechanism for gas using a logging tool such as the MRIL-C.

Transverse relaxation time, $T_2$, in a magnetic field gradient is a function of bulk relaxation, surface relaxation, and diffusion according to:

$$\frac{1}{T_2} = \frac{1}{T_{2B}} + \frac{1}{T_{2S}} + \frac{1}{T_{2D}} \quad (4)$$

Using a CPMG sequence, the relaxation time due to diffusion ($T_{2D}$) is:

$$T_{2D} = \frac{3}{\gamma^2 G^2 D t_{CP}^2} \quad (5)$$

where $\gamma$ is the $^1$H gyromagnetic ratio (26,741 radians/s-gauss), D is the diffusion coefficient, G is the field gradient created by the NMR tool, and $t_{CP}$ is half of the interecho time. This is the predominate relaxation mechanism for the gas phase. From Equations 4 and 5, it can also be seen that $t_{cp}$ could be increased to an extent that $1/T_{2d}$ is the dominate, or controlling relaxation mechanism.

The diffusion coefficient of a gas in a formation is limited on a upper limit by unrestricted diffusion, and at a lower limit by restricted diffusion.

The unrestricted diffusion coefficient, $D_o$ of supercritical methane as a function of temperature and density can be found, for example, in Gerritsma et al., supra, and also in Dawson et al., *AIChE Journal*, Vol 16, No. 5, 1970. Under typical reservoir conditions, methane will have a density of about 0.2 g/cc, and a diffusion coefficient about 50 times that of water, or about $109 \times 10^{-5}$ cm$^2$/s compared to $2 \times 10^{-5}$ cm$^2$/s for water. Thus, using Equation (5), if unrestricted bulk diffusion occurred, with the MRIL C logging tool (G=17 gauss/cm, $t_{CP}$=0.6 ms), $T_{2D}$ would equal 37.1 ms.

A ratio of the restricted diffusion coefficient, D', over the unrestricted diffusion coefficient, $D_o$ approaches a limit of the inverse of the tortuosity as the fluids diffuse through many pores. Tortuosity is defined as the product of the formation resistivity factor, F, and the formation porosity, $\phi$. The formation resistivity factor can be determined, for example, using an induction log, and the porosity can be determined from a neutron log.

In the practice of the present invention, it is not necessary to know the diffusion coefficient, D, with accuracy to determine the pore volume occupied with hydrocarbon gas because the hydrocarbon gas response is shifted by alteration of $t_{cp}$ in the present invention. Pore volume filled by gas is identified by the difference between two NMR logs.

The range of transverse relaxation times within which a hydrocarbon gas peak is to be expected in an NMR log can therefore be anticipated using Equation 4 and Equation 5, because the hydrocarbon gas is not a surface-wetting phase, as:

$$\frac{1}{T_2} = \frac{1}{T_{2B}} + \frac{\gamma^2 G^2 t_{cp}^2 D}{3} \quad (7)$$

Rearranging Equation 7 and recalling from above that $T_1 = T_{1B} \approx T_{2B}$:

$$\frac{1}{T_2} = \frac{1}{T_1}\left(1 + \frac{\gamma^2 G^2 t_{cp}^2 D T_1}{3}\right) \quad (8)$$

The interecho time $t_{cp}$ can therefore be calculated that would result in the range within which $T_2$ for the hydrocarbon gas would be within a detectable range. For a MRIL C logging tool, with typical reservoir conditions, a $t_{cp}$ of about 0.6 ms would result in a measured $T_2$ being about 40 ms. The NMR porosity indicated by this log would therefore include porosity filled with hydrocarbon gas. Another NMR log using a CPMG sequence having a different interecho time than the first NMR log preferably uses an $t_{cp}$ that results in the $T_2$ due to the hydrocarbon gas being less about 2.5 ms. For a MRIL C logging tool, with typical reservoir conditions, a $t_{cp}$ of about 2.4 ms would be sufficient to result in a $T_2$ below detectable limits of a tool such as the MRIL-C. The difference between the NMR porosities from two such logs, divided by the effective hydrogen index at formation conditions, would be the hydrocarbon gas content of the formation because the second log would not detect the hydrocarbon gas.

In order to remove $T_2$ bias, one should use only a subset of the echoes obtained under the short $t_{cp}$ sequence which occur at the same times as the echoes obtained under the long $t_{cp}$ sequence. Thus if $t_{cp2}$ is four times $t_{cp1}$, one would use only every fourth echo in the $t_{cp1}$ sequence.

In the practice of the present invention, it is not necessary that a multiexponential inversion be performed on echo data obtained from the NMR logging tool. Rather than the results of the multiexponential inversion, subtracting integrals of the time domain echo responses yields a result that is proportional to the gas-filled porosity, $\phi_g$, (when an interecho time is used that is long enough to suppress $T_2$ of the gas peak below detection in one of the two logs, $2t_{cp2}$, and an interecho time short enough to result in a measurable $T_2$ of the hydrocarbon gas peak, $2t_{cp1}$). Utilizing the difference between the integrals of the time domain echo responses is preferable because noise is more directly canceled. This can be seen starting with equations for measured decay curves as functions of time:

$$A_1(t) = S_1(t) + N_1(t) \quad (9)$$

$$A_2(t) = S_2(t) + N_2(t) \quad (10)$$

where: $A_1(t)$ is the measured decay curve obtained using $t_{cp1}$;
$A_2(t)$ is the measured decay curve obtained using $t_{cp2}$;
$S_1(t)$ is the signal of the decay curve without noise for the log using $t_{cp1}$;
$S_2(t)$ is the signal of the decay curve without noise for the log using $t_{cp2}$;
$N_1(t)$ is noise in the measured decay curve using $t_{cp1}$; and
$N_2(t)$ is noise in the measured decay curve using $t_{cp2}$.

Noise is assumed to be random thermal noise which has the same expectation value on both passes. Therefore:

$$\int N_1(t)dt - \int N_2(t)dt = 0 \quad (11)$$

Integrating the two measured decay curves $A_1(t)$ and $A_2(t)$ from a time $t_0$, which is much less than $T_2$ of the hydrocarbon gas, $T_{2g}$, with $t_{cp1}$, and greater than $T_2$ of the hydrocarbon gas with $t_{cp2}$, to $T_0$ which is much greater than $T_{2g}$ at $t_{cp1}$ results in the cancellation of the integrals of $N_1(t)$ and $N_2(t)$ according to:

$$\int_{t_0}^{T_0} A_1(t)dt - \int_{t_0}^{T_0} A_2(t)dt = \int_{t_0}^{T_0} [S_1(t) - S_2(t)]dt \quad (12)$$

Because the only change between the two logging scans is the interecho time $2t_{cp}$ which was altered to make hydrocarbon gas undetectable in one of the two logging scans, the difference between the two measured decay curves is the decay curve attributable to the hydrocarbon gas decay. This hydrocarbon gas decay curve, g(t), is one of the decay curves of the summation of Equation 1, which can be expressed as:

$$g(t) = \alpha HI \phi_g e^{-\frac{t}{T_{2g}}} \quad (13)$$

Integration of this function from $t_0$ to $T_0$ results in:

$$\int_{t_0}^{T_0} [S_1(t) - S_2(t)]dt = -\alpha HI \phi_g T_{2g}\left[\frac{1}{e^{-\frac{T_0}{T_{2g}}}} - \frac{1}{e^{-\frac{t_0}{T_{2g}}}}\right] \quad (14)$$

Because to is much less than $T_{2g}$ and $T_0$ is much greater than $T_{2g}$:

$$\frac{1}{e^{-\frac{T_0}{T_{2g}}}} - \frac{1}{e^{-\frac{t_0}{T_{2g}}}} \cong -1 \quad (15)$$

Therefore, Equations 14 and 12 can be solved for $\phi_g$:

$$\phi_g = \frac{\int_{t_0}^{T_0} A_1(t)dt - \int_{t_0}^{T_0} A_2(t)dt}{\alpha HI T_{2g}} \quad (16)$$

Another alternative is to extrapolate an echo decay curve to time (or number of echo) equal to zero. The signal amplitude at zero time is also proportional to NMR porosity. These alternatives eliminate the need to do the multiexponential inversion.

The TABLE below lists typical $T_1$, $T_2$, HI, $D_o$ and $D_o T_1$ for brine, oil and natural gas. The values of $T_2$ are for the MRIL-C tool with a gradient of about 17 gauss/cm and $t_{cp}$ of 0.6 ms. The TABLE shows that the $T_1$ of oil and natural gas may overlap despite a large $T_2$ contrast. One can also see from the TABLE that brine and oil may have overlapping $D_o$ or $T_2$, but distinctly separated $T_1$. Because $D_o T_1$ of gas is an order of magnitude greater than oil, and two orders of magnitude greater than brine, one can see from Equation 8 that the already large $DT_1$ contrast of gas can be enhanced by increasing the interecho time $2t_{cp}$ in order to allow the separation of two fluids (such as oil and hydrocarbon gas) that overlap in $T_1$.

TABLE

|  | $T_1$ ms | $T_2$ ms | HI | $D_0 \times 10^{-5}$ cm²/s | $D_0 T_1$ cm² |
|---|---|---|---|---|---|
| brine | 1 to 500 | 0.67 to 200 | 1 | 7.7 | 0.0077 to 4 |
| oil | 5000 | 460 | 1 | 7.9 | 40 |
| gas | 4400 | 40 | 0.38 | 100 | 440 |

From the TABLE and Equation 8, it can be seen that the present invention can be applied to determine porosities filled with liquid hydrocarbons, or hydrocarbon gas plus liquid hydrocarbons by increasing $t_{cp}$ to a time that causes $T_2$ of both the hydrocarbon gas and the liquid hydrocarbon to shift. The significant difference between $D_o T_1$ of brine and oil indicates that a range of $t_{cp}$s could be determined wherein the $T_2$ peak of the liquid hydrocarbons has shifted significantly whereas the $T_2$ peak of brine is still relatively unaffected compared to a NMR log using a different $t_{cp}$. Thus the method of the present invention can be used to determine the porosity of a formation filled with gas, liquid hydrocarbon, or gas plus liquid hydrocarbon by simply integrating time domain responses of NMR logs using different $t_{cp}$s.

When compared to prior art method of determine hydrocarbon liquid content of a formation, i.e., performing a multiexponential inversion of time domain responses and distinguishing based on the location of $T_2$ peaks, the present method more directly cancels noise. Further, considerably less computing capacity or data storage is required because of elimination of the multiexponential inversion.

The MRIL C tool has a depth-of-investigation of 16 inches. In an eight inch diameter borehole, the formation can therefore be examined up to four inches of the bore hole wall Oil-based muds have low invasion to this depth and are therefore the preferred drilling mud for practice of this invention. With low invasion oil-based muds the gas saturation observed by the MRIL C logging tool will be substantially unflushed. In particular, ESCAID 110 oil-based drilling mud with 80% ESCAID 110 and 20% CaCl2-saturated water to provide very little invasion in Gulf of Mexico sands and is therefore a preferred system.

EXAMPLE

Figure 4:
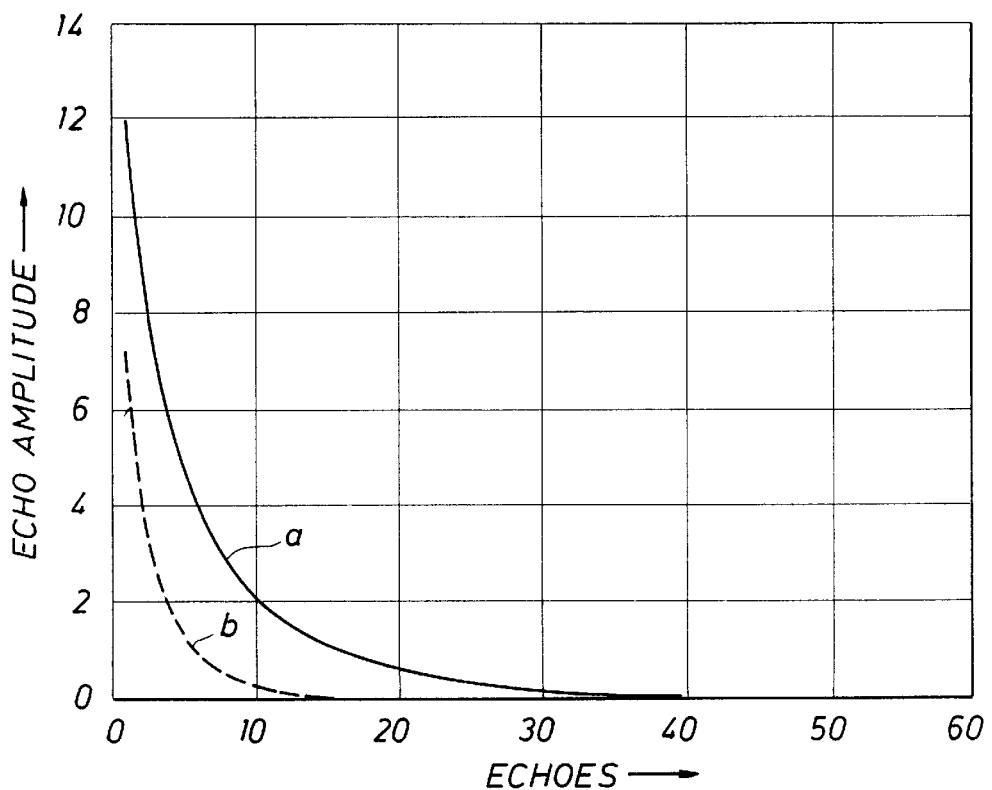
FIG. 4 is a plot of $T_2$ decay curves for a gas bearing formation using interecho times of $1.2 \times 10^{-3}$ and $4.8 \times 10^{-3}$ seconds.

A numerical simulation was performed of two logs of a formation with a MRIL C tool, with a $T_W$ of eight seconds, and $t_{cp}$'s of 0.6 and 2.4 ms. FIG. 4 is a plot of echo vs. echo amplitude for both logs, with line "a" representing the log with $t_{cp}$ of 0.6 ms and line "b" representing the log with $t_{cp}$ of 2.4 ms. The formation was a gas reservoir at irreducible conditions with capillary bound water-filled porosity of 10 p.u. and gas-filled porosity of 20 p.u. The NMR properties for the gas phase are those in the TABLE. Only every fourth echo from the log using a $t_{cp}$ of 0.6 ms was used to eliminate $T_2$ bias. Also, the first two echoes from the resulting CPMG sequences were discarded.

Figure 5:
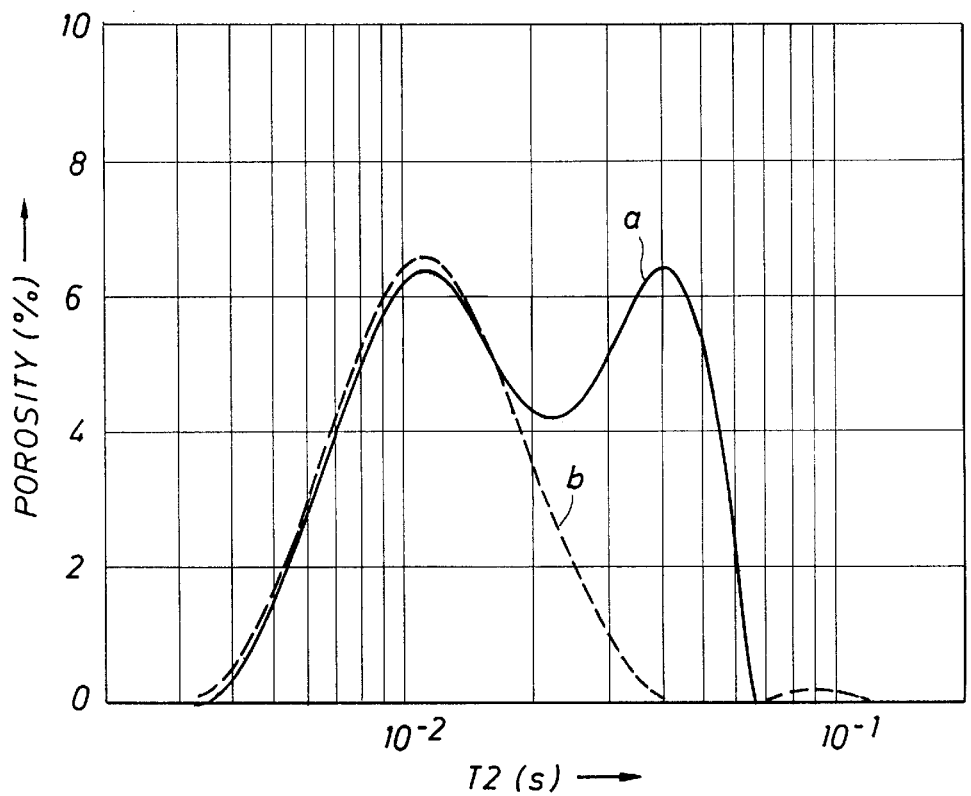
FIG. 5 is a plot of $T_2$ spectra obtained from an inversion of the $T_2$ decay curves of FIG. 4.

FIG. 5 is a plot of NMR porosity, in percent, vs. $T_2$ calculated from the decay curves of FIG. 4, with lines a and b representing the porosity measured using 0.6 and 2.4 ms interecho times respectively. It can be seen from FIG. 5 that a distinct peak from the gas phase centered at about 40 ms is prevalent in the log using the $t_{cp}$ of 0.6 ms whereas this peak is not present in the log using the $t_{cp}$ of 2.4 ms. From FIG. 5 it can be seen that the longer $t_{cp}$ has shifted the gas spectrum below deductibility, leaving only the brine signal, centered at 12 ms, in the spectrum. The difference between the integrals of the area under these curves therefore represents the NMR porosity attributable to hydrocarbon gas.

We claim:

1. A method to estimate the formation pore volume occupied by hydrocarbon gasp the method comprising the steps of:

obtaining a first pulsed NMR log of the formation, the first NMR log utilizing a pulse sequence comprising an initial 90° radio frequency pulse, followed by a series of 180° radio frequency pulses starting at a time period $t_{cp2}$ after the initial 90° pulse, and the series of 180° pulses comprising radio frequency pulses each separated by a time $2t_{cp2}$ wherein the time $t_{cp2}$ is a time that is greater than that which results in the measured transverse relaxation time of the hydrocarbon gas being less than about $2 \times 10^{-3}$ seconds;

obtaining a second pulsed NMR log of the formation, the second NMR log utilizing a pulse sequence comprising an initial 90° radio frequency pulse, followed by a series of 180° pulses starting at a time period $t_{cp1}$ after the initial 90° pulse, and the series of 180° pulses comprising radio frequency pulses each separated by a time $2t_{cp1}$ wherein the time $t_{cp1}$ is a time that is less than that which results in the measured transverse relaxation time of the hydrocarbon gas being greater than about $4 \times 10^{-3}$ seconds;

determining from the first and the second NMR logs the pore volume of a formation occupied by hydrocarbon gas.

2. The method of claim 1 wherein the pore volume of the formation occupied by hydrocarbon gas is determined by:

determining, from the first and the second NMR logs, a distribution of transverse relaxation times attributable to hydrocarbon gas within the formation; and determining from the distribution of transverse relaxation times attributable to hydrocarbon gas within the formation the pore volume of a formation occupied by hydrocarbon gas within the formation.

3. The method of claim 1 wherein $t_{cp1}$ is less than that which results in the measured transverse relaxation time of the hydrocarbon gas being greater than about $8 \times 10^{-3}$ seconds.

4. The method of claim 1 wherein $t_{cp2}$ is equal to or greater than about 2.4 ms.

5. The method of claim 1 wherein $t_{cp1}$ is equal to or less than about 0.6 ms.

6. The method of claim 1 wherein the two logs are obtained at the same time by a tool utilizing different pulse sequences in two annuli located slightly apart from each other.

7. The method of claim 1 wherein both the first and the second log are obtained using pulse sequences wherein $T_W$ is about six seconds or more.

8. The method of claim 2 wherein $t_{cp2}$ is equal to or greater than about 2.4 ms.

9. The method of claim 8 wherein $t_{cp1}$ is equal to or less than about 0.6 ms.

10. The method of claim 9 wherein the two logs are obtained at the same time by a tool utilizing different pulse sequences in two annuli located slightly apart from each other.

11. The method of claim 10 wherein both the first and the second log are obtained using pulse sequences wherein $T_W$ is about six seconds or more.

12. A method to estimate a formation pore volume occupied by hydrocarbon gas utilizing a NMR logging tool, the method comprising the steps of:

obtaining a first pulsed NMR log of the formation, the first NMR log utilizing a pulse sequence comprising an initial 90° radio frequency pulse, followed by a series of 180° radio frequency pulses starting at a time period $t_{cp1}$ after the initial 90° pulse, and the series of 180° pulses comprising radio frequency pulses each separated by a time $2t_{cp1}$ wherein the time $t_{cp1}$ is a time which results in the measured transverse relaxation time of the hydrocarbon gas being within a range of measured transverse relaxation times that are detectable with the NMR logging tool utilized;

obtaining a second pulsed NMR log of the formation, the second NMR log utilizing a pulse sequence comprising an initial 90° radio frequency pulse, followed by a series of 180° radio frequency pulses starting at a time period $t_{cp2}$ after the initial pulse, and the series of 180° pulses comprising radio frequency pulses each separated by a time period $2t_{cp2}$ wherein the time $t_{cp2}$ is a time that is different from $t_{cp1}$ by an amount of time sufficient to separate resultant peaks of transverse relaxation times attributable to hydrocarbon gas within the formation; and determining from the first and the second NMR logs the formation pore volume occupied by hydrocarbon gas.

13. The method of claim 12 wherein the formation pore volume occupied by hydrocarbon gas is determined by:

determining, from the first and the second NMR logs, a distribution of transverse relaxation times attributable to hydrocarbon gas within the formation; and determining from the distribution of transverse relaxation times attributable to hydrocarbon gas within the formation the pore volume of a formation occupied by hydrocarbon gas within the formation.

14. The method of claim 12 wherein $t_{cp1}$ is less than that which results in the measured transverse relaxation time of the hydrocarbon gas being greater than about $8 \times 10^{-3}$ seconds.

15. The method of claim 12 wherein $t_{cp2}$ is equal to or greater than about 2.4 ms.

16. The method of claim 12 wherein $t_{cp1}$ is equal to or less than about 0.6 ms.

17. The method of claim 12 wherein the two logs are obtained at the same time by a tool utilizing different pulse sequences in two annuli located slightly apart from each other.

18. The method of claim 12 wherein both the first and the second log are obtained using pulse sequences wherein $T_W$ is about six seconds or more.

19. The method of claim 12 wherein $t_{cp2}$ of the second log is sufficiently long that the measured transverse relaxation time of the hydrocarbon gas is below detectable limits of the NMR logging tool.

20. The method of claim 12 wherein the second log is performed using a $T_W$ that is less than $T_1$ of the hydrocarbon gas at formation conditions.

21. A method to estimate a formation pore volume occupied by a hydrocarbon phase or phases utilizing a NMR logging tool, the method comprising the steps of:

obtaining a first pulsed NMR log of the formation, the first NMR log utilizing a pulse sequence comprising an initial 90° radio frequency pulse, followed by a series of 180° radio frequency pulses starting at a time period $t_{cp1}$ after the initial 90° pulse, and the series of 180° pulses comprising radio frequency pulses each separated by a time $2t_{cp1}$ wherein the time $t_{cp1}$ is a time which results in the measured transverse relaxation time of the hydrocarbon phase or phases being within a range of measured transverse relaxation times that are detectable with the NMR logging tool utilized;

obtaining a second pulsed NMR log of the formation, the second NMR log utilizing a pulse sequence comprising an initial 90° radio frequency pulse, followed by a series of 180° radio frequency pulses starting at a time period $t_{cp2}$ after the initial pulse, and the series of 180° pulses comprising radio frequency pulses each separated by a time period $2t_{cp2}$ wherein the time $t_{cp2}$ is a time that is different from $t_{cp1}$ by an amount of time sufficient to separate resultant peaks of transverse relaxation times attributable to the hydrocarbon phase or phases within the formation; and determining from the first and the second NMR logs the formation pore volume occupied by the hydrocarbon phase or phases.

22. The method of claim 21 wherein the formation pore volume occupied by the hydrocarbon phase or phases is determined by:

determining, from the first and the second NMR logs, a distribution of transverse relaxation times attributable to hydrocarbon phase or phases within the formation; and determining from the distribution of transverse relaxation times attributable to hydrocarbon phase or phases within the formation the pore volume of a formation occupied by hydrocarbon gas within the formation.

23. The method of claim 21 wherein $t_{cp1}$ is less than that which results in the measured transverse relaxation time of the hydrocarbon gas being greater than about $8 \times 10^{-3}$ seconds.

24. The method of claim 21 wherein $t_{cp2}$ is equal to or greater than about 2.4 ms.

25. The method of claim 21 wherein $t_{cp1}$ is equal to or less than about 0.6 ms.

26. The method of claim 21 wherein the two logs are obtained at the same time by a tool utilizing different pulse sequences in two annuli located slightly apart from each other.

27. The method of claim 21 wherein both the first and the second log are obtained using pulse sequences wherein $T_W$ is about six seconds or more.

28. The method of claim 21 wherein $t_{cp2}$ of the second log is sufficiently long that the measured transverse relaxation time of the hydrocarbon phase or phases is below detectable limits of the NMR logging tool.

29. The method of claim 28 wherein the formation pore volume occupied by the hydrocarbon phase or phases is determined as a function of the difference between the integrals of the time domain responses of the two NMR logs.

* * * * *